United States Patent [19]

Fee et al.

[11] Patent Number: 5,298,751

[45] Date of Patent: * Mar. 29, 1994

[54] REMOTE ACTIVE VAPOR CONCENTRATION MEASUREMENT SYSTEM AND METHOD THEREOF

[75] Inventors: Maurice L. Fee, Anaheim; Robert B. Lyons, Placentia; Michael A. Truman, Anaheim, all of Calif.

[73] Assignee: Aerojet-General Corporation, Rancho Cordova, Calif.

[*] Notice: The portion of the term of this patent subsequent to Mar. 15, 2011 has been disclaimed.

[21] Appl. No.: 854,219

[22] Filed: Mar. 20, 1992

[51] Int. Cl.⁵ .............................................. G01N 21/35
[52] U.S. Cl. .................................. 250/338.5; 250/339; 250/341
[58] Field of Search .................... 250/338.5, 340, 339, 250/341

[56] References Cited

U.S. PATENT DOCUMENTS

| | | | |
|---|---|---|---|
| 3,662,171 | 5/1972 | Brengeman et al. | 250/338.5 |
| 3,843,258 | 10/1974 | Shupe | 250/573 |
| 4,489,239 | 12/1984 | Grant et al. | 250/339 |
| 4,496,839 | 1/1985 | Bernstein et al. | 250/341 |
| 4,529,317 | 7/1985 | Cramp | 250/339 |

OTHER PUBLICATIONS

Brassington, "Photo-acoustic Detection and Ranging-A New Technique for the Remote Detection of Gases", J. Phys. D: Appl. Phys., 15 (2), Feb. 1982, pp. 219-228.

Primary Examiner—Carolyn E. Fields
Attorney, Agent, or Firm—Leonard Tachner

[57] ABSTRACT

A remote vapor concentration measurement system comprising a unitary, single-fixed wavelength laser to heat the background surface behind a vapor or gas cloud, the constituents of which are to be detected and measured. A heated background acts as a broad band infrared source for measuring absorption characteristics of the gas or vapor constituents. A spectrally responsive receiver, which for example may be a spectrometer or radiometer having filters at selected wavelengths corresponding to the absorption characteristics of the specie of gas or vapor being detected, is also provided. This receiver measures the relative absorbance of infrared energy at selected wavelengths over a relatively broad infrared range to measure the absorbance characteristics of the specie of gas or vapor of interest. The system also comprises a range finder positioned adjacent the receiver for measuring the distance between the receiver and the background surface along two different paths. The respective paths provide two different distances through the vapor or gas cloud. The concentration of the vapor or gas cloud or constituent thereof may be readily ascertained from two such measurements along such different paths. Concentration of the constituent equals the difference in respective absorbances of the constituent measured along said two different paths, divided by the product of the absorption coefficient of the constituent and the difference in the length along said paths within the vapor or gas cloud.

6 Claims, 3 Drawing Sheets

REMOTE ACTIVE VAPOR CONCENTRATION MEASUREMENT SYSTEM AND METHOD THEREOF

BACKGROUND OF THE INVENTION

1. Field of the Invention

The present invention relates generally to remote concentration measurement of gases and vapors and more specifically to a remote active vapor concentration measurement system and method thereof in which a range finder is integrated with a remote vapor detection system to permit the measurement of the concentrations of vapors or gases. Such a system allows an accurate assessment of the danger of explosion or toxicity to humans or animals. A remote vapor detection system that may be used in conjunction with the range finder of the present invention is disclosed in co-pending patent application Ser. No. 07/844,524, filed on Mar. 2, 1992 in the name of Maurice Fee, a co-inventor of the present invention.

2. Prior Art

U.S. Pat. No. 4,529,317 to Cramp is directed to a method of monitoring gaseous pollutants. Using laser scanning apparatus, two intersecting scanning beams, coordinated by a central control unit, provide the information necessary to determine the concentration of a known pollutant. Two helium-neon lasers provide a detection beam and a non-absorbed reference beam at a nearby wavelength. The detection and reference beams are passed through choppers and to power meters. Power meters continuously monitor the power output of the lasers. The radiation is detected by a detector and the information furnished to a computer as the central control unit. With this information, the position and/or concentration of the particular pollutant can be determined.

U.S. Pat. No. 3,843,258 to Shupe is directed to a dual beam absorption spectrometer useful for determining the concentration of atmospheric pollutants. The figure illustrates the dual beam absorption spectrometer having signal generating apparatus for providing two coherent wave energy signals, namely, laser signals. Measuring apparatus is provided to receive and measure the intensities of the signals provided after they have traversed a sample containing region. A first signal has a wavelength slightly offset from a second signal so that it will not be absorbed by the predetermined material. In operation, a spectrometer can be used as a field instrument to measure the concentration of a predetermined material along paths of several thousand feet, or several miles.

U.S. Pat. No. 4,496,839 to Bernstein et al is directed to a system for identification of chemical species by laser initiated infrared spectroscopy. The laser is directed at a chemical mass which absorbs energy at the laser wavelength and the absorbed laser energy is re-emitted giving rise to a non-resonant infrared emission spectrum of the chemical species. The identity, as well as its range and concentration, may be established by comparison of its spectrum to that for known species. The system is diagrammed in FIG. 1 of Bernstein et al, showing a $CO_2$ infrared laser passed through a suitable optic system to the unknown chemical species. The returning radiation is separated by a monochromator into three wavelengths which are then sensed by detectors. The outputs of detectors are delivered to a data acquisition circuit which compares the intensity of the collected radiations from which the identity and concentrations may be determined.

U.S. Pat. No. 4,489,239 to Grant et al is directed to a portable remote laser sensor for methane leak detection. This system is capable of detection of methane and for further determination of concentration thereof. This invention includes a pair of helium-neon gas lasers operating continuously at two wavelengths. The two laser beams are chopped and are directed at the area in which gas detection is to occur. The laser radiation is collected and passed to the optical detector. The detector measures the difference between the two signals and the methane concentration is measured using the differential absorption Lidar technique.

Accordingly, it will be seen that the most relevant prior art known to the applicant includes a patent which requires two specific laser wavelengths to detect the gas of interest and two sites of displaced lasers and receivers. It also includes a patent in which a two specific laser wavelength system only provides average concentration along the total path length. Another particular prior art patent uses a high power laser pulse to excite the specie of interest and measure the wavelengths of the re-emitted radiation for specific identification. By timing between the excitation pulse and a re-emitted pulse, the range is determined. The claim to concentration measurement is based on the return signal from an unknown, compared to the signal from a known quantity. This type of concentration measurement would have to be an average type over some path with large uncertainties. The remaining patents described above, all provide average concentrations over a path length. Using these devices, one could be in an apparent safe area, based on an average measurement of path length, where as the local concentration might actually be lethal. The only two types of systems that provide specific and not path average concentration measurements, are the differential absorption systems using back-scatter from the atmospheric constituents and a system that uses two displaced laser/receiver systems.

There is therefore an ongoing need for a remote active vapor concentration measurement system which overcomes the aforementioned deficiencies of the prior art.

SUMMARY OF THE INVENTION

The aforementioned ongoing need is satisfied by the present invention which avoids all of the previously noted deficiencies of the prior art by integrating a range finder and a remote vapor detection system which utilizes only a single laser wavelength to heat the background behind the vapor or gas of interest and thus increase the infrared radiation of the background. The invention remotely determines the concentration of vapor or gas. The system operates on the premise that if two absorption measurements are taken through a gas or vapor cloud along different path lengths, then with accurate range information one can remotely determine the concentration of the gas or vapor in question. The system uses a range finder adjacent to and co-aligned with a remote vapor detection system receiver to provide accurate range information. Absorption data and range information are input into a processor which calculates the concentration of the constituent gas or vapor and then displays the result to the user. A description of the remote vapor detection system used in the present invention is provided in co-pending patent application Ser. No. 07/844,524, the contents of which are hereby incorporated herein by reference. Generally, the detection system laser operates at a wavelength which is not absorbed by the vapor or gas of interest. Furthermore, the receiver compares the infrared energy at wavelengths which would be absorbed by the vapor or gas of interest, with energy in a reference band in which the vapor or gas of interest is not generally absorbed. The receiver may be, for example, a spectrometer or a radiometer having at least one filter centered at a wavelength known to be absorbed by the vapor or gas of interest and at least one filter centered at a wavelength not absorbed by the vapor or gas of interest. The present invention may be implemented with detection systems other than the system disclosed in the aforementioned co-pending patent application.

OBJECTS OF THE INVENTION

It is therefore a principal object of the present invention to provide a remote active vapor concentration measurement system and method thereof which is more sensitive and less complex than prior art vapor concentration measurement systems.

It is an additional object of the present invention to provide a remote active vapor concentration measurement system and method thereof which utilizes a unitary, low power, single fixed wavelength laser as an energy source to provide a broad band absorption detection measurement and a range finder to determine the path length for each such measurement in order to calculate the concentration of the detected vapor or gas constituent.

It is still an additional object of the present invention to provide a remote active vapor concentration measurement system and method thereof which unlike the prior art, does not provide only average concentration along a total path length and does not require two different displaced laser/receivers to determine the path lengths through the gas; furthermore, it does not use a detector system which relies on back-scatter or fluorescence or the heating of vapor or gas cloud itself to make the detection measurement.

It is still an additional object of the present invention to provide a remote active vapor concentration measurement system and method thereof which employs a single, fixed wavelength laser of relatively low power to heat the background surface behind the vapor cloud or gas to be detected; a spectrally responsive receiver for measuring absorption characteristics of the gas or vapor species, based upon a broad band infrared source provided by the heated background surface and a range finder for determining the path length over which the detection system operates during each such measurement for calculating the concentration of the gas or vapor of interest.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which.

DETAILED DESCRIPTION OF A PREFERRED EMBODIMENT

Figure 1:
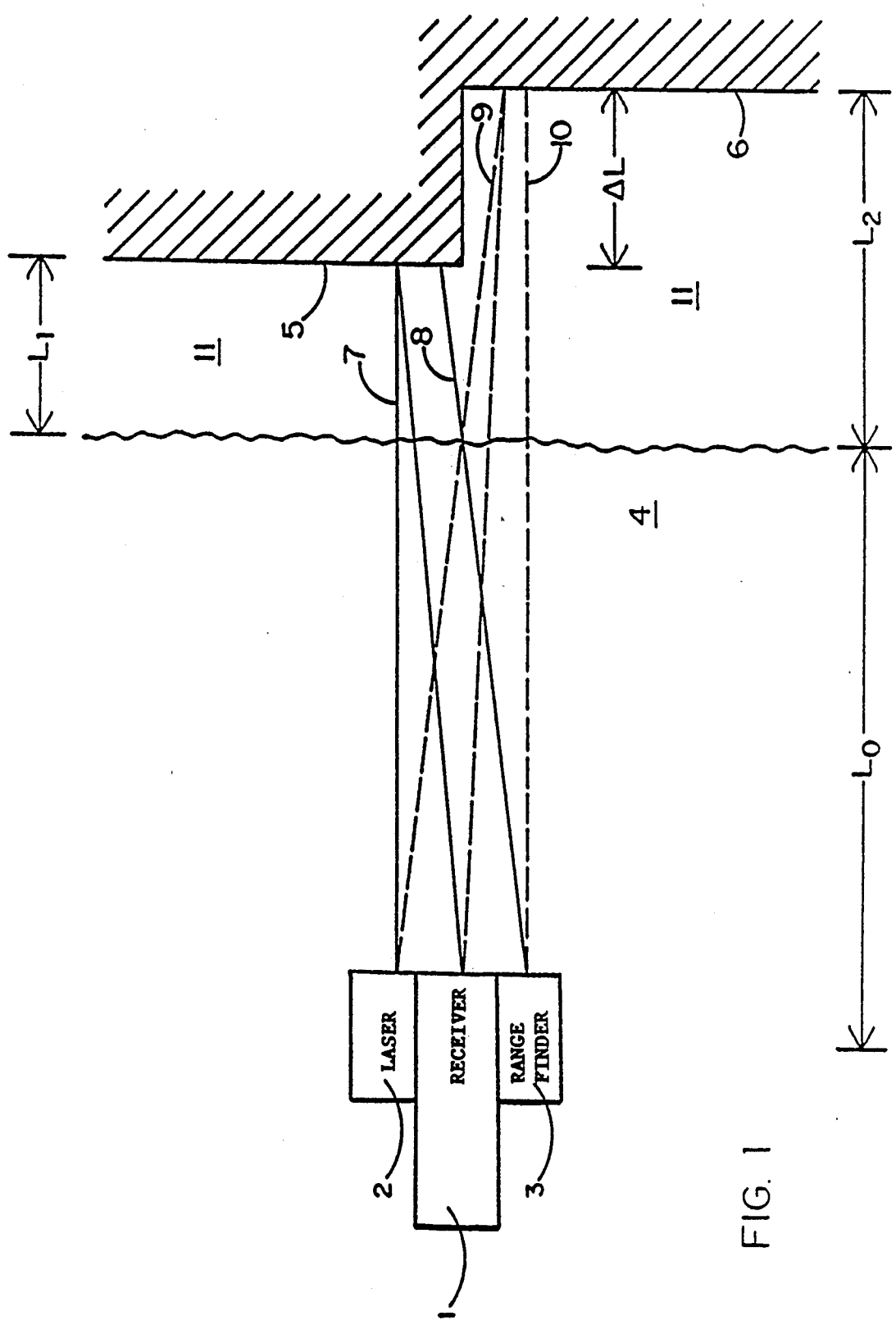
FIG. 1 is a simplified block diagram of a configuration of the system of the present invention, illustrating the integral background heating concept and range determination features thereof.

The concept of the present invention may be understood best by referring to FIG. 1 in which it will be seen that a vapor cloud 11 is in the presence of a background structure 5 and 6, such as buildings or terrain. A range finder 3 is co-aligned with a wavelength selective infrared receiver 1 to provide accurate range information. The system, which is comprised of the assembly of the receiver 1, the energy source or laser 2, and a range finder 3, is positioned a distance $L_0$ back from the vapor boundary 4. Two absorption readings $\sigma_1$ and $\sigma_2$ are taken in sequence along paths 7 and 9, respectively. One reading, $\sigma_1$, utilizes background 5 and passes through a distance $L_1$ of the vapor and the distance $(L_0+L_1)$ is obtained by means of the range finder 3. The second absorption reading, $\sigma_2$, uses background 6 and passes through a distance $L_2$ of the same vapor cloud. The distance $(L_0+L_2)$ is measured by the range finder 3. From molecular absorption theory, $\sigma_1 = \alpha C L_1$ and $\sigma_2 = \alpha C L_2$, where C is the concentration of gas or vapor in parts per million, $\alpha$ is the absorption coefficient for the particular gas or vapor in parts per million meters and o is the absorbance of the vapor or gas. From the range finder measurements along the respective paths through the vapor, $\Delta L$ can be determined as follows:

$$\Delta L \text{ equals } (L_0+L_2)-(L_0+L_1)=(L_2-L_1).$$

The difference in absorbances $\sigma_2-\sigma_1=\alpha C\Delta L$. Therefore, the concentration C of the vapor is equal to $\sigma_2-\sigma_1$, divided by $\alpha\Delta L$.

Thus, it will be seen that by taking two sequential measurements over different path lengths through the same vapor cloud or gas cloud, one may readily calculate the concentration level of the gas or vapor cloud constituent the absorbance of which has facilitated the detection thereof.

Figure 2:
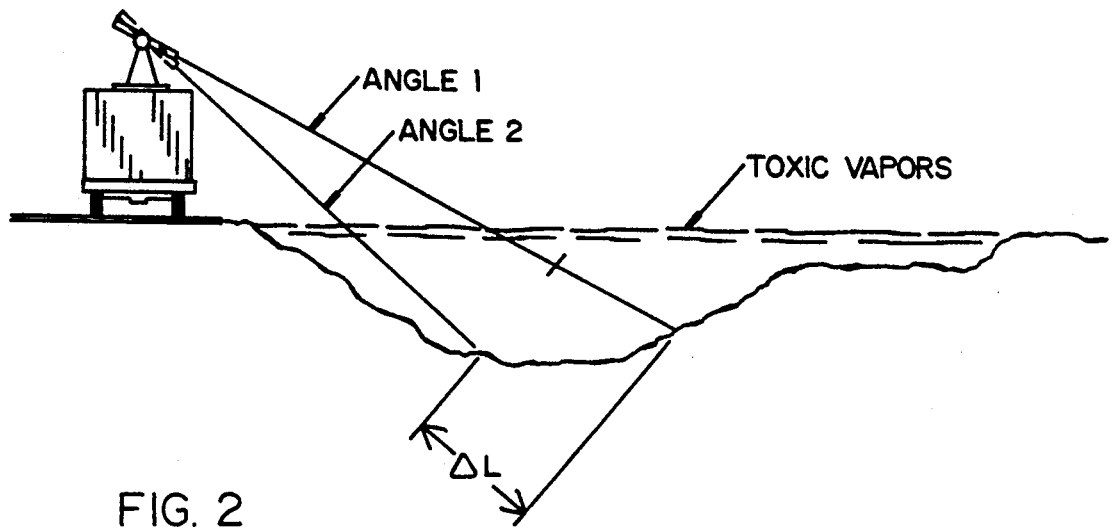
FIG. 2 is a conceptual drawing which illustrates the use of the present invention for measuring vapor concentration of suspected illegally dumped toxic waste.

In FIG. 2, a ground mobile vapor concentration measurement system is illustrated near suspected, illegally dumped toxic waste wherein a pit-like background surface provides the broad band infrared radiation source for measuring the absorbance of the suspected toxic waste gas or vapor. The vapor concentration measurement system, which like that shown in FIG. 1, comprises a laser, a spectrally responsive receiver and a range finder, is mounted in a mobile unit which can detect vapors or gases and measure the range to the background through two different angles from one position, thus providing two different path lengths through the suspected toxic waste gas or vapor and thereby permitting the calculation described previously in conjunction with FIG. 1.

In the event that there is a background surface which precludes obtaining absorption detection over two different path lengths through the vapor cloud or gas from one location via angular changes one may also acquire the data necessary to calculate the concentration of the gas or vapor by changing the position of the integrated range finder and absorbance detection system of the present invention parallel to the vapor cloud or gas boundary so that the path length through the vapor cloud or gas is altered from one position to the other. An example of this repositioning concept is illustrated in the application shown in FIG. 3.

Figure 3:
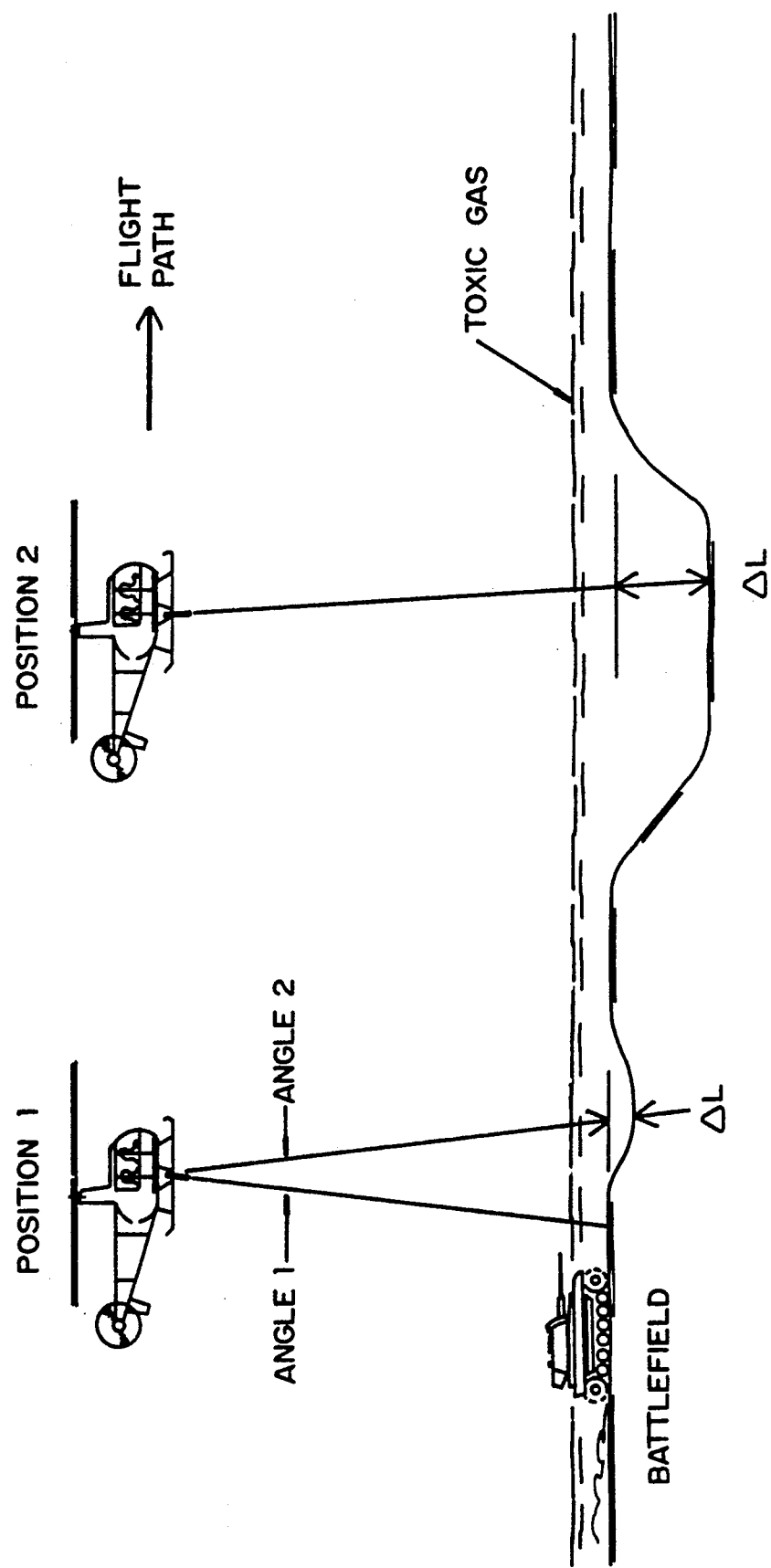
FIG. 3 is an illustrative drawing of the present invention illustrating its use in a battlefield environment to measure vapor concentration of toxic gases.

FIG. 3 illustrates both fixed platform with angular change for obtaining ΔL, and moving platform with no angular change for obtaining ΔL concepts for a battlefield situation in which a helicopter provides the platform for the remote vapor concentration measurement system of the present invention and the battlefield ground, for example, provides the requisite background surface for heating and thus creating a broad band infrared source. Toxic gas that may be emitted from a tank or which may comprise the environment in which a friendly tank is positioned, can be readily measured using two different angles and positions, thus providing the differential path lengths ΔL through the suspected toxic gas cloud for measurement of the concentration thereof.

Figure 4:
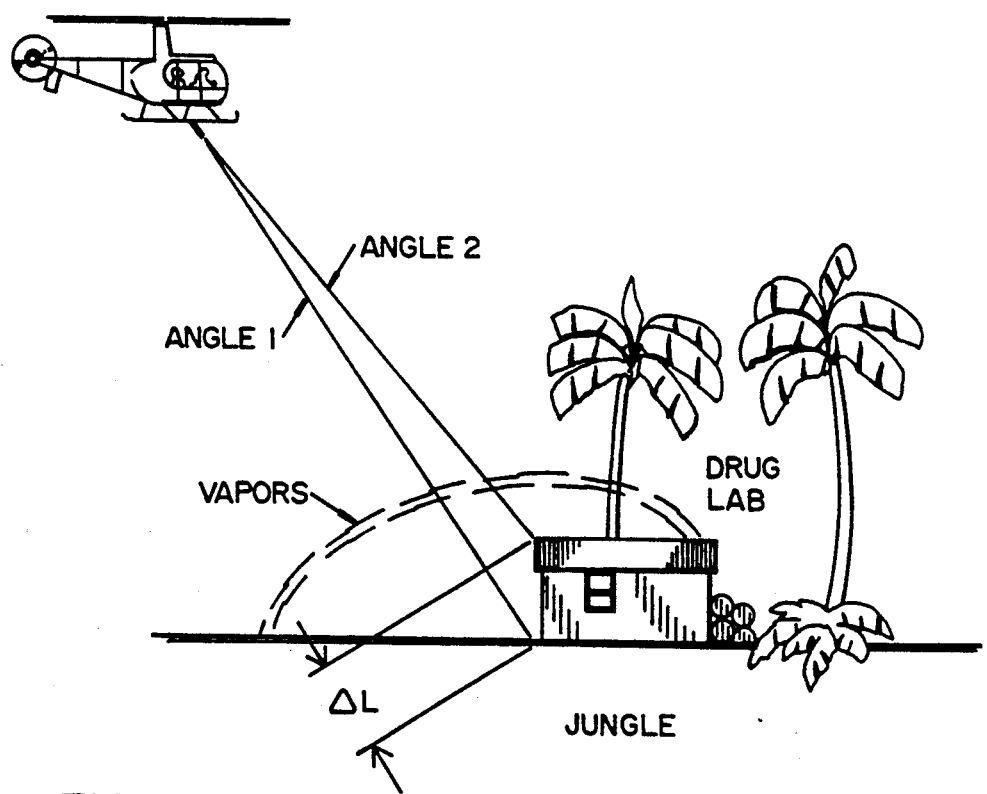
FIG. 4 is an illustrative conceptual drawing of the present invention shown being used for the remote measurement of vapor concentration at a suspected drug laboratory.

FIG. 4 illustrates a concept for a suspected drug laboratory, wherein a helicopter-based system of the present invention can be used to measure suspected gas leakage concentrations from the suspected drug laboratory from two different angles so that the requisite data for alternative path lengths can also be provided in this example.

It will now be understood that what has been disclosed herein comprises a novel remote vapor concentration measurement system comprising a unitary, single-fixed wavelength laser to heat the background surface behind a vapor or gas cloud, the constituents of which are to be detected and measured. A heated background acts as a broad band infrared source for measuring absorption characteristics of the gas or vapor constituents. A spectrally responsive receiver, which for example may be a spectrometer or radiometer having filters at selected wavelengths corresponding to the absorption characteristics of the specie of gas or vapor being detected, is also provided. This receiver measures the relative absorbance of infrared energy at selected wavelengths over a relatively broad infrared range to measure the absorbance characteristics of the specie of gas or vapor of interest. The receiver thus identifies the gas specie based upon an absorption "fingerprint" and permits determination of the absorption coefficient of that specie such as by "look-up" table. The system also comprises a range finder positioned adjacent to the receiver for measuring the distance between the receiver and the background surface along two different paths. The respective paths provide two different distances through the vapor or gas cloud. The different path lengths may be obtained by changing the angle of the measurement, relative to the background surface so that different portions of the background surface are relied upon for each path measurement through the vapor or gas cloud, each such portion of the background surface being a different distance from the spectrally responsive receiver and range finder. An alternative method for altering the path lengths through the vapor or gas cloud is to position the laser, the receiver and the range finder on a mobile platform, which can then readily re-position those elements of the vapor concentration system of the present invention so that the length measured through the vapor or gas cloud to the background surface is different along each such path. Moving the mobile platform in level flight such as by a helicoptor can also be used by relying on variations in the thickness of a gas below caused by variations in background structure. In any case, the concentration of the vapor or gas cloud or constitutent thereof may be readily ascertained from two such measurements along such different paths. Concentration of the constituent equals the difference in respective absorbances of the constituent measured along said two different paths, divided by the product of the absorption coefficient of the constituent and the difference in the length along said paths within the vapor or gas cloud.

Those having skill in the art to which the present invention pertains, will now as a result of the applicants' teaching herein, perceive various modifications and additions which may be readily made to the invention. By way of example, while the aforementioned spectrally sensitive receiver and range finder have been illustrated herein as separate components of the system, it may be advantageous to combine the two into one instrument, or for that matter to combine the laser or other heating source into the same instrument to provide a unitary remote sensor system for measuring vapor concentration having all of the requisite components described herein integrated into one assembly. Accordingly, all such modifications and additions shall be deemed to be within the scope of the present invention which is to be limited only by the claims appended hereto and their equivalents.

We claim:

1. A system for remotely measuring the concentration of at least one constituent of a vapor or gas located adjacent to background surfaces; the system comprising:

a laser generating a beam of energy directed to said surfaces for heating said surfaces to a temperature higher than the temperature of said vapor or gas, said higher temperature causing said surfaces to radiate infrared energy through said vapor or gas;

a spectrally sensitive receiver positioned for receiving said infrared energy after said infrared energy has passed through said vapor or gas along two different paths of different respective lengths in said vapor or gas, a portion of said infrared energy having been absorbed at certain wavelengths along each said different path, said certain wavelengths of absorption identifying said at least one constituent of which the concentration is to be measured; and a range finder adjacent said receiver for measuring the distance between said receiver and said surfaces along said two different paths.

2. The system recited in claim 1 wherein said laser generating said beam of energy operates at a wavelength which is substantially not absorbed by said at least one constituent.

3. The system recited in claim 1 wherein said spectrally sensitive receiver comprises a spectrometer operating at infrared wavelengths.

4. The system recited in claim 1 wherein said spectrally sensitive receiver comprises a radiometer and at least one band pass filter having a center frequency corresponding to one of said certain wavelengths.

5. The system recited in claim 1 wherein said spectrally sensitive receiver comprises a measurement frequency band and a reference frequency band for comparing energy in each said respective frequency band.

6. A remote vapor concentration system comprising:
a remote vapor detection device for remotely identifying the constituents of a cloud of gas or vapor;
a range finder substantially co-located with said detection device for measuring at least two different path lengths through said cloud; and
means for calculating the concentration C of each constituent according to the formula $$C = \frac{\sigma_2 - \sigma_1}{\alpha \Delta L}$$

where $\sigma_2$ and $\sigma_1$ are the respective absorbances of a constituent measured along said different path lengths $\alpha$ is the absorption coefficient of said constituent and $\Delta L$ is the difference in said path lengths.

* * * * *